United States Patent
Lee et al.

(10) Patent No.: US 7,663,758 B2
(45) Date of Patent: Feb. 16, 2010

(54) APPARATUS AND METHOD FOR DETECTING SURFACE PLASMON RESONANCE

(75) Inventors: Ju Yi Lee, Taipei (TW); Hsueh-Ching Shih, Taipei (TW); Cyun Tai Hong, Taipei (TW)

(73) Assignee: Industrial Technology Research Institute, Hsinchu County (TW)

( * ) Notice: Subject to any disclaimer, the term of this patent is extended or adjusted under 35 U.S.C. 154(b) by 408 days.

(21) Appl. No.: 11/760,356

(22) Filed: Jun. 8, 2007

(65) Prior Publication Data
US 2008/0158549 A1    Jul. 3, 2008

(30) Foreign Application Priority Data
Dec. 27, 2006   (TW) ............................... 95149149 A

(51) Int. Cl.
G01N 21/55    (2006.01)
(52) U.S. Cl. ...................................... 356/445
(58) Field of Classification Search ............... None
See application file for complete search history.

(56) References Cited

U.S. PATENT DOCUMENTS

| | | | |
|---|---|---|---|
| 5,994,150 A * | 11/1999 | Challener et al. ........... 356/428 |
| 6,384,916 B1 * | 5/2002 | Furtak ......................... 356/369 |
| 6,515,745 B2 * | 2/2003 | Vurens et al. ............... 356/369 |
| 6,980,294 B2 * | 12/2005 | Namba et al. ............... 356/318 |
| 7,339,681 B2 * | 3/2008 | Su et al. ...................... 356/491 |
| 2003/0219809 A1 | 11/2003 | Chen et al. |
| 2006/0197952 A1 * | 9/2006 | Chen et al. ................... 356/445 |

\* cited by examiner

*Primary Examiner*—Gregory J Toatley, Jr.
*Assistant Examiner*—Juan D Valentin
(74) *Attorney, Agent, or Firm*—WPAT, P.C.; Anthony King

(57) ABSTRACT

An apparatus for detecting surface plasmon resonance (SPR) comprises a light source, a light-coupling unit, a phase-resolving module, and a data-processing unit. The light source provides a light beam emitting into a surface of a metal film to generate surface plasmon resonance. The phase-resolving module is configured to split the reflection light of the light beam on the surface of the metal film into a first light, a second light, a third light, and a fourth light, and to detect the intensities of the lights simultaneously. The phases of the first light and second light differentiate by 90 degrees, and the phases of the third light and fourth light differentiate by 90 degrees. The data-processing unit calculates the phase variation of the surface plasmon resonance on the metal film based on the intensities of the first light, second light, third light, and fourth light.

14 Claims, 11 Drawing Sheets

APPARATUS AND METHOD FOR DETECTING SURFACE PLASMON RESONANCE

BACKGROUND OF THE INVENTION (A) Field of the Invention

The present invention relates to an apparatus and a method for detecting surface plasmon resonance (SPR). More particularly, the present invention relates to an image-phase apparatus and a method for detecting the SPR.

(B) Description of the Prior Art

The physical characteristics will change slightly while there are inter biomolecules interactions happening on the surface of bio-thinfilm. If such tiny physical change can be detected by certain means of technique, the techniques became a method of analyzing biomolecular interactions.

With the development and combination of optical technology and Micro-Electro-Mechanical Systems (MEMS), various biosensing technologies have been developed, for example, Confocal Laser Scanning Fluorescence microscopy (CLSFM), Quartz Crystal Micro-balance (QCM), Surface Plasmon Resonance (SPR), etc. Among them, SPR technology has the highest sensitivity of interfacial bio-interactions.

Since B. Liedberg applied the SPR principle to detect air composition in 1983, analyzers based on SPR have been widely and successfully applied in various research fields. For example, SPR technology and biochips are combined for the application of biomedical detection, in which it is not necessary to use the fluorescent labeling. Moreover, it can detect fast detection and has high sensitivity, and can replace the fluorescent labeling method in certain applications.

According to the working principle, SPR technology is usually classified into the following categories: (1) Detection of resonant angle by angle modulation; (2) Detection of a resonant wavelength by a light wavelength modulation; (3) Intensity detection; and (4) Phase-sensing. According to prior research papers, the resolution for angle modulation or light wavelength modulation to the refractive index is approximately $10^{-5}$ refractive index unit (RIU), and the resolution for the phase-sensing is higher, which approached up to $10^{-7}$ RIU. The angle modulation method or the light wavelength modulation method is simple and is used in most of the current SPR instruments. However, as the concentration of the sample to be detected is becoming lower and lower and users generally demanding for higher resolution, phase detection method with a high resolution has become the current trend for technical development. On the other hand, fast detecting and filtering are the future trend for biomolecular sensing, and full-field imaging analysis is also one of the crucial points in the development.

U.S. Patent Application No. 2003/0219809, filed by Chen Shean-Jen et al., discloses a PZT phase-shifting method used in obtaining the phase difference of the SPR phenomenon, and the system architecture is an SPR detecting apparatus 10, as shown in FIG. 1. A light beam emitted by a laser light source 11 is split into two lights through a polarizing plate 12 and a light beam amplifier 13, and the two lights are incident into a prism 14, and a reflection occurs on a surface of a metal film 15 adjacent to the prism 14. The two reflection lights emit to a light-emitting diode (LED) 18 through beam splitters 16, 17 and a lens 21. In addition, the reflection light is split into another two lights towards a PZT driving element 19 through the beam splitter 16, and then received by a charge-coupled device (CCD) 22 through a ½ wave plate 23, a beam splitter 20, and another lens 21. Then, according to an optical signal received by the CCD device 22, a mathematical operation is used to obtain phase differences of the object to be detected. The disadvantage of this method lies in the fact that the price of the current PZT driving element is relatively high, and a high voltage power source is required for the PZT element, so the cost of the instrument will increase.

Furthermore, for the current SPR phase-detecting technologies, a heterodyne light source together with a lock-in amplifier is mostly used to obtain the phase, or a piezoelectric actuator together with a five-step phase-shifting method is used to obtain the phase. For the above two processes, the fabricating method is complex and the building cost for the instrument is relatively high. In addition, as to the five-step phase-shifting method, it is necessary to take five images to calculate a set of meaningful data, so sampling time is relatively long.

SUMMARY OF THE INVENTION

The present invention provides a full-field image phase-detecting technique using SPR, so as to measure, for example, a biomolecular reaction. In the present invention, there is no need for a PZT driving element or a multi-wavelength light source, and a phase can be obtained without performing correction and compensation, thereby simplifying the apparatus and reducing the cost.

The SPR detection apparatus of the present invention includes a light source, a light-coupling unit, a phase-resolving module, and a data-processing unit. The light source provides a light beam emitting to a surface of a metal film of the light-coupling unit to generate SPR. The phase-resolving module splits a reflection light of the light beam on the surface of the metal film into a first light, a second light, a third light, and a fourth light, and detects the intensities of the lights simultaneously. The phases of the first light and second light differentiate from each other by 90 degrees, and the phases of the third light and fourth light differentiate by 90 degrees. The data-processing unit calculates phase variation of SPR on the surface of the metal film based on the intensities of the first light, second light, third light, and fourth light.

From a perspective of a detecting method, the above SPR detection comprises: (1) providing a light beam emitting to the surface of the metal film for generating the SPR; (2) splitting the reflection light of the light beam on the surface of the metal film into four lights; the phases of the four lights are classified into two groups, and the phases of two lights in each group differentiate by 90 degrees; (3) simultaneously detecting the intensities of the four lights; and (4) calculating phase variation of SPR generated on the surface of the metal film based on the intensities.

According to the SPR detection of the present invention, the light intensity signals of four phases are taken, and the phase to be detected is calculated by a numerical method similar to the five-step phase-shifting method on principle. The advantage of this method lies in the fact that the objective of resolving the phase can be achieved merely through utilizing optical elements, i.e., there is no need for additional light sources or driving mechanisms, thereby reducing manufacturing costs, and decreasing fabrication and subsequent maintenance difficulties. In addition, unlike the five-step phase-shifting method that needs to take images five times to obtain the signal, the present invention takes required images once, so that sampling time can be reduced. Compared with the former cases, the present invention resolves the phase without performing correction and compensation, and therefore, it is simpler and more precise.

DETAILED DESCRIPTION OF THE INVENTION

Figure 1:
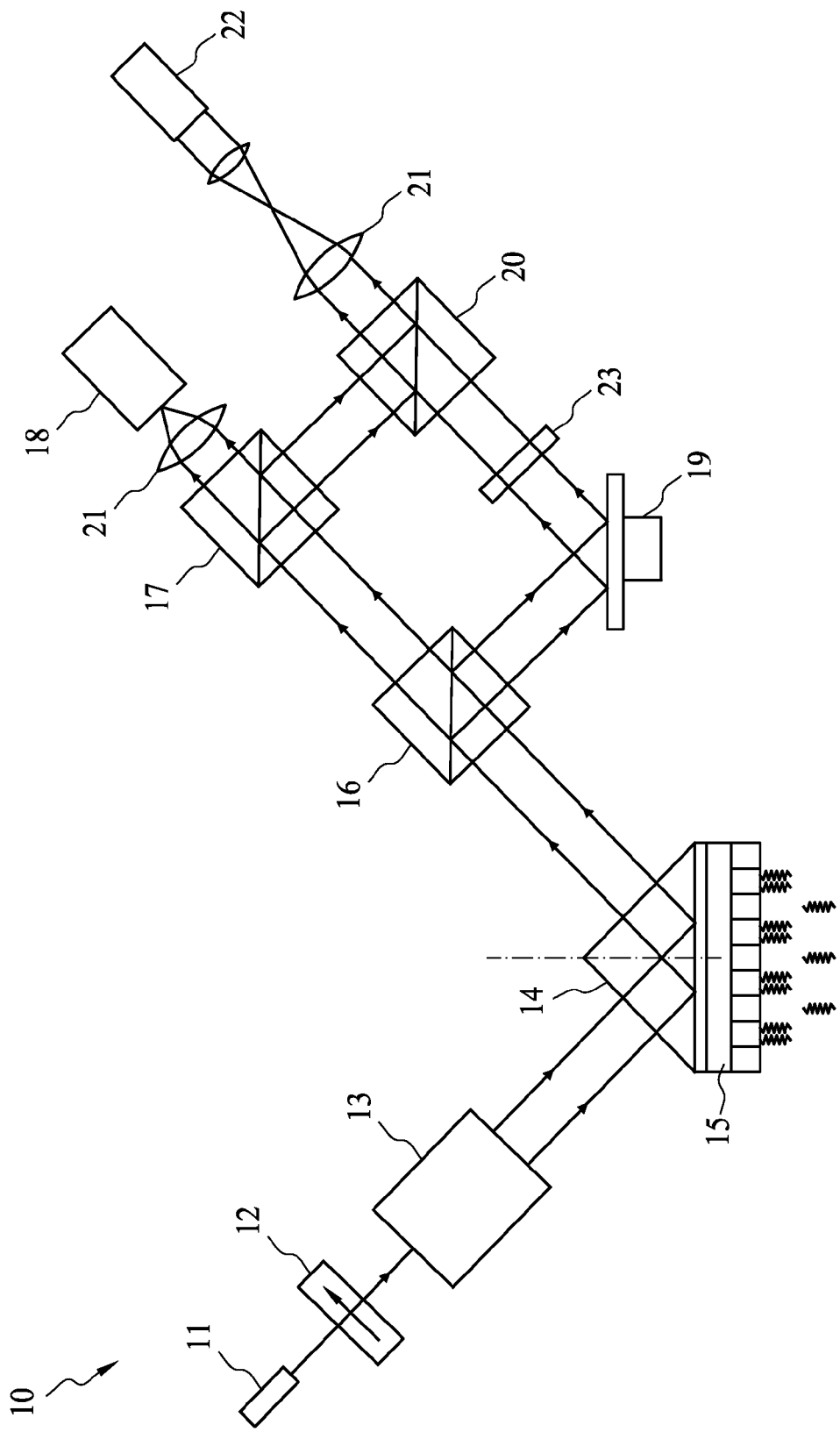
FIG. 1 shows a known SPR detecting apparatus.

The present invention is described in detail below according to the sequence of basic principles, system architecture of phase-resolving technique, theoretical analysis, and refractive index distribution simulation.

Basic Principles

SPR occurs between a dielectric material and a metal film, and the horizontal polarization component (P polarized light) of the incident light source energizes free electrons of the metal film to generate the longitudinal resonance movement, and this movement is transferred along a medium surface, which is surface plasmon wave (SPW). According to the SPR theory, if the horizontal component $k_x$ of the wave vector $k_0$ for the P polarized light is equal to the wave vector $k_{sp}$ of the SPW, SPR is generated, as in the following formula (1):

$$k_x = k_0 \varepsilon_g(\lambda)\sin(\theta) = k_0 \sqrt{\frac{\varepsilon_m(\lambda) \cdot n^2}{\varepsilon_m(\lambda) + n^2}} = k_{sp}, \quad (1)$$

$\theta$ indicates an incident angle, $\lambda$ indicates a wavelength of an incident light, $\varepsilon_g(\lambda)$ indicates a dielectric coefficient of the coupling prism, $\varepsilon_m(\lambda)$ indicates a dielectric coefficient of the metal film, $k_0$ indicates a wave vector in the vacuum, and n indicates a refractive index of an object to be detected.

The prism coupling method of Kretschmann is used to excite SPR, and according to the Fresnel equation and the multi-reflection theory, the reflection coefficient $r_p$ of the P polarized light and the reflection coefficient $r_s$ of the S polarized light are obtained through the following equations:

$$r_p = \frac{r^p_{12} + r^p_{23}\exp(2ik_{z2}d_2)}{1 + r^p_{12}r^p_{23}\exp(2ik_{z2}d_2)} = |r_p|e^{i\phi_p}, \quad (2)$$

$$r_s = \frac{r^s_{12} + r^s_{23}\exp(2ik_{z2}d_2)}{1 + r^s_{12}r^s_{23}\exp(2ik_{z2}d_2)} = |r_s|e^{i\phi_s}, \quad (3)$$

wherein $$r^p_{ij} = \frac{\varepsilon_j k_{zi} - \varepsilon_i k_{zj}}{\varepsilon_j k_{zi} + \varepsilon_i k_{zj}},$$

$$r^s_{ij} = \frac{k_{zi} - k_{zj}}{k_{zi} + k_{zj}},$$

$$k_{zi,j} = [\varepsilon_{i,j}(k_0)^2 - k_1^2]^{0.5},$$

$$k_1 = k_0\sin(\theta)\varepsilon_1^{0.5}, \; i,j = 1, 2, 3$$

$\phi_p$ and $\phi_s$ indicate phases of the P polarized light and the S polarized light, respectively, and the phase difference $\Phi$ is $$\Phi = \phi_p - \phi_s \quad (4),$$

$k_{zi,j}$ represents the corresponding wave vector in z direction, $k_1$ is $k_x$ of Equation (1), $r_{ij}^q$ indicates a Fresnel reflection coefficient of the $i^{th}$ layer and the $j_{th}$ layer, the superscripts represent the P polarized light or the S polarized light, i or j is randomly 1 (prism $\varepsilon_1$), 2 (metal film $\varepsilon_2$), and 3 (layer to be detected $\varepsilon_3$). Because $\varepsilon_3 = n_2$, the refractive index variation of the sample layer to be detected is reflected, and thus, the reaction situation of the biomolecular bond is derived.

Figure 2:
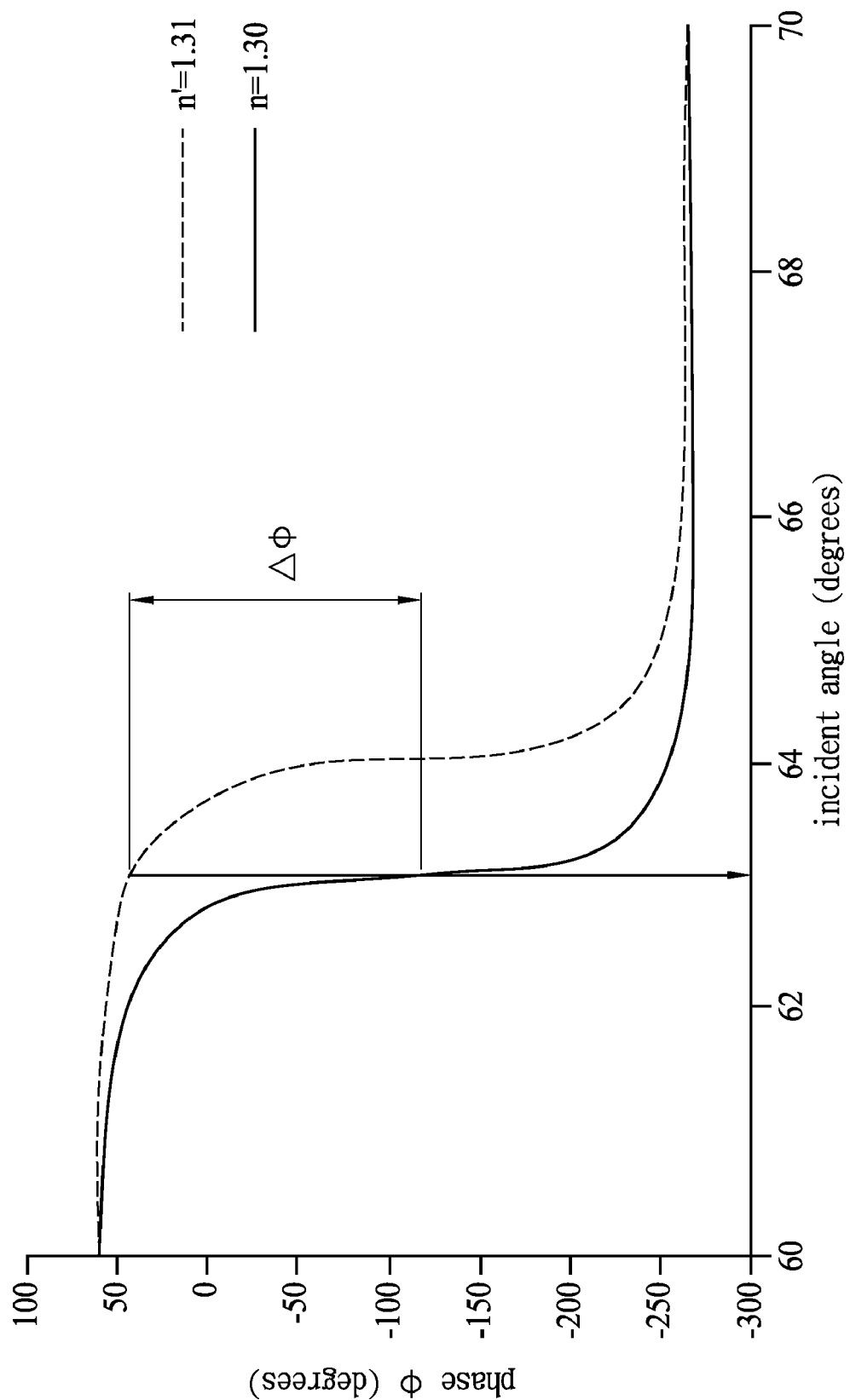
FIG. 2 shows the relationship between phases and incident angles for different refractive indexes.

The Equations (2), (3), and (4) are substituted in the program for simulation, and the relevant parameters are listed as follows: a wavelength of the incident light of 785 nm, an angle scope between 60-70 degrees, a thickness of the metal film of 50 nm, dielectric constants of $\varepsilon_1 = 2.27$, $\varepsilon_2 = -23.45 + 1.242i$, n=1.3, and n'=1.31. The relationship between the phase variation and the incident angle is shown in FIG. 2.

If the incident angle is fixed at 63.2 degrees, the phase value corresponding to the refractive index n=1.3 of the object to be detected is approximately −115 degrees. If the refractive index is changed to n'=1.31, the corresponding phase value is approximately +41 degrees, and the phase variation $\Delta\Phi$ is approximately 156 degrees. If the resolution of the phase-resolving technique is $\Delta R = 0.01$, the system sensitivity $\Delta S$ can be obtained through the following equation (5):

$$\Delta S = \frac{\partial n}{\partial \Phi}\Delta R = 6 \times 10^{-7} RIU. \quad (5)$$

Phase-resolving Technique (a) System Architecture

Figure 3:
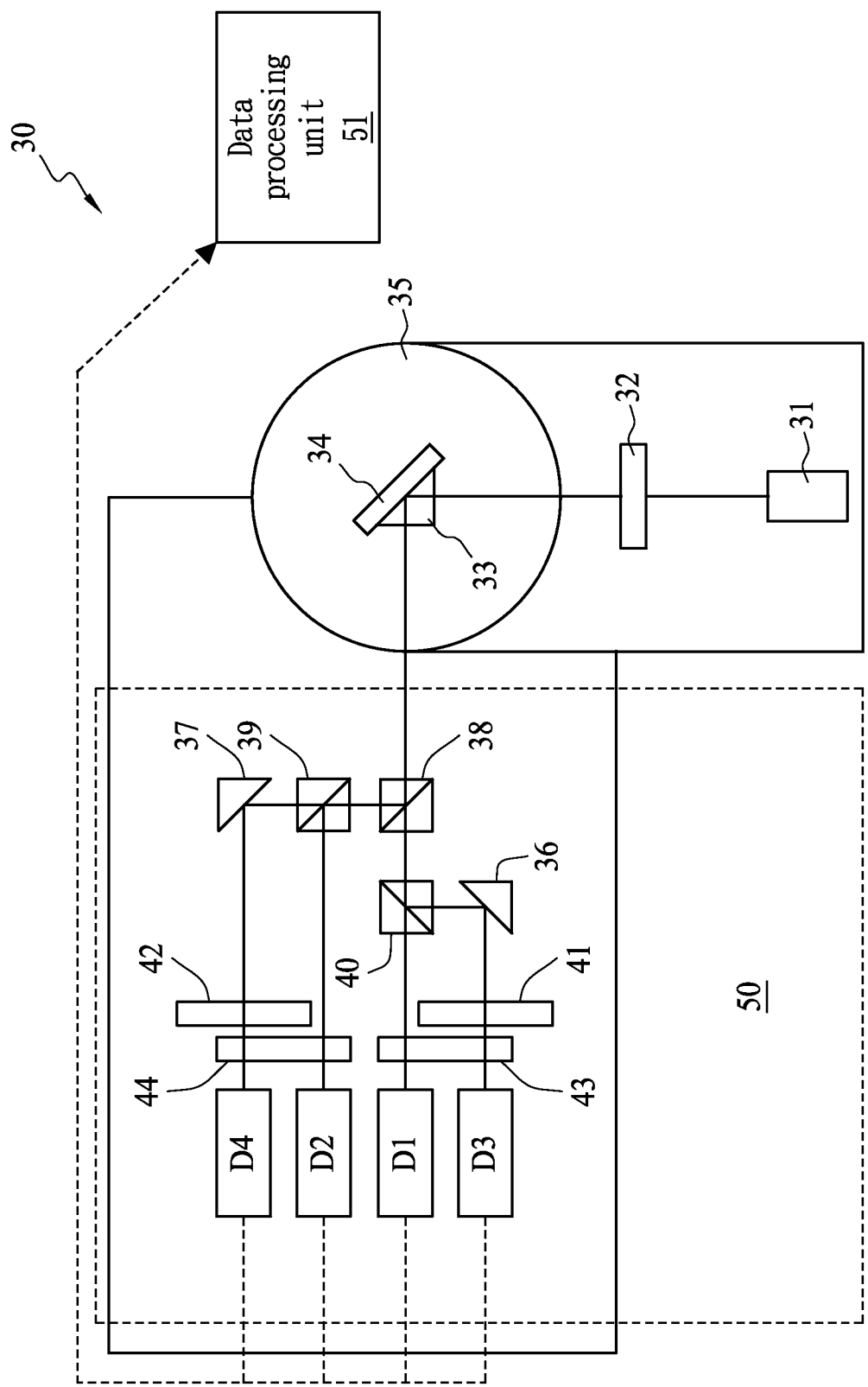
FIG. 3 shows a SPR detection apparatus in accordance with the present invention.

FIG. 3 shows an SPR detection apparatus 30 in accordance with the present invention. The apparatus 30 includes a light source 31, a polarizing plate 32, a prism 33, a phase-resolving module 50, and a data-processing unit 51. The phase-resolving module 50 includes beam splitters 38, 39 and 40, reflecting mirrors 36 and 37, ¼ wave plates 41 and 42, analyzers 43 and 44, and light detectors D1, D2, D3, and D4. In this embodiment, the light detectors D1, D2, D3 and D4 are CCD sensing elements. The data-processing unit 51 is a computer or a microprocessor.

The light source 31 of this embodiment employs a diode laser with a wavelength of 785 nm (a wideband white light source also can be used), the generated light beam emits to the polarizing plate 32 to adjust the components of a P polarized light and an S polarized light, and then emits into the prism 33. A reflection occurs on the surface of the metal film 34 neighboring the prism 33, and the incident angle is controlled by the rotating mechanism 35. An object to be detected, for example, a biochip, is disposed on the other surface of the metal film 34 opposite the prism 33.

The light from the prism 33 is split into two rays through the beam splitter 38. One ray is further split into two rays through a beam splitter 40, in which one ray directly passes through the analyzer 43 with a polarizing angle of 45 degrees, and then is projected to the light detector D1; the other ray changes the traveling direction through the reflecting mirror 36, and sequentially passes through the ¼ wave plate 41 and the analyzer 43, and is finally received by the light detector D3.

The other ray split by the beam splitter 38 is further split into two rays via another beam splitter 39. One ray directly passes through the analyzer 44 with the polarizing angle of −45 degrees; the other ray is reflected by the reflecting mirror 37, and then sequentially passes through the ¼ wave plate 42 and the analyzer 44. Finally, the two rays are received by the light detectors D2 and D4, respectively. The rays received by light detectors D1, D2, D3 and D4 are deemed a first light, a second light, a third light and fourth light for subsequent analysis.

(b) Jones Matrix Theory Analysis

Jones Matrix is employed to calculate the intensities of the lights received by the light detectors D1, D2, D3 and D4. First, the reflecting electric field magnitude $E_{SPR}$ of the light from the prism 33 is considered, $$E_{SPR} = r_{SPR} \cdot E_{in} \qquad (6)$$
$$= \begin{pmatrix} |r_p|e^{i\phi_p} & 0 \\ 0 & |r_s|e^{i\phi_s} \end{pmatrix} \begin{pmatrix} \cos\alpha \\ \sin\alpha \end{pmatrix}$$
$$= \begin{pmatrix} \cos\alpha |r_p|e^{i\phi_p} \\ \sin\alpha |r_s|e^{i\phi_s} \end{pmatrix},$$

$r_{SPR}$ is the reflection coefficient of the incident light caused by SPR system, and $E_{in}$ is the electric field amplitude of the incident light. Once the SPR occurs, P polarizing reflection light is too small, so the contrast is relatively low. Consequently, the components of the P polarized light and the S polarized light of the incident light can be adjusted by rotating the polarizing angle of the polarizing plate 32, and thereby, the components can be adjusted to be the same in order to increase the contrast.

In order to make $\cos\alpha |r_p|=a$ and $\sin\alpha |r_s|=b$, Equation (6) is changed to Equation (7):

$$E_{SPR} = \begin{pmatrix} ae^{i\phi_p} \\ be^{i\phi_s} \end{pmatrix}. \qquad (7)$$

The intensities of the lights respectively received by four light detectors D1, D2, D3, and D4 are considered below.

$E_1$ is the electric field amplitude of the reflection light passing through the analyzer 43 with the polarizing angle of 45 degrees and received by the light detector D1:

$$E_1 = A1 \cdot E_{SPR} = \begin{pmatrix} 1 & 1 \\ 1 & 1 \end{pmatrix} \begin{pmatrix} ae^{i\phi_p} \\ be^{i\phi_s} \end{pmatrix} = (ae^{i\phi_p} + be^{i\phi_s})\begin{pmatrix} 1 \\ 1 \end{pmatrix}. \qquad (8)$$

The intensity $I_1$ of the light is $$I_1 = |E_1|^2 = a^2 + b^2 + 2ab\cos(\phi_p - \phi_s) \qquad (9).$$

$E_2$ is the electric field amplitude of the reflection light passing through the analyzer 44 with the polarizing angle of −45 degrees and received by the light detector D2, $$E_2 = A2 \cdot E_{SPR} = \begin{pmatrix} 1 & -1 \\ -1 & 1 \end{pmatrix} \begin{pmatrix} ae^{i\phi_p} \\ be^{i\phi_s} \end{pmatrix} = (ae^{i\phi_p} - be^{i\phi_s})\begin{pmatrix} 1 \\ 1 \end{pmatrix}. \qquad (10)$$

The intensity $I_2$ of the light is $$I_2 = |E_2|^2 = a^2 + b^2 - 2ab\cos(\phi_p - \phi_s) \qquad (11).$$

$E_3$ is the electric field amplitude of the reflection light firstly passing through the ¼ wave plate 41 with a fast axis of 90 degrees, then passing through the analyzer 43 with the polarizing angle of 45 degrees, and received by the light detector D3, $$E_3 = A3 \cdot Q \cdot E_{SPR} = \begin{pmatrix} 1 & 1 \\ 1 & 1 \end{pmatrix}\begin{pmatrix} 1 & 0 \\ 0 & i \end{pmatrix}\begin{pmatrix} ae^{i\phi_p} \\ be^{i\phi_s} \end{pmatrix} = (ae^{i\phi_p} - bie^{i\phi_s})\begin{pmatrix} 1 \\ 1 \end{pmatrix}. \qquad (12)$$

The intensity $I_3$ of the light is:

$$I_3 = |E_3|^2 = a^2 + b^2 + 2ab\sin(\phi_p - \phi_s) \qquad (13)$$

$E_4$ is the electric field amplitude of the reflection light firstly passing through the ¼ wave plate 42 with a fast axis of 90 degrees, then passing through the analyzer 44 with the polarizing angle of −45 degrees, and received by the light detector D4.

$$E_4 = \qquad (14)$$
$$A4 \cdot Q \cdot E_{SPR} = \begin{pmatrix} 1 & -1 \\ -1 & 1 \end{pmatrix}\begin{pmatrix} 1 & 0 \\ 0 & i \end{pmatrix}\begin{pmatrix} ae^{i\phi_p} \\ be^{i\phi_s} \end{pmatrix} = (ae^{i\phi_p} - bie^{i\phi_s})\begin{pmatrix} 1 \\ 1 \end{pmatrix}.$$

The intensity $I_4$ of the light is:

$$I_4 = |E_4|^2 = a^2 + b^2 - 2ab\sin(\phi_p - \phi_s) \qquad (15).$$

$I_X$ is obtained by subtracting Equation (11) from Equation (9), $$I_X = I_1 - I_2 = 4ab\cos(\phi_p - \phi_s) \qquad (16).$$

$I_Y$ is obtained by subtracting Equation (15) from Equation (13).

$$I_Y = I_3 - I_4 = 4ab\sin(\phi_p - \phi_s) \qquad (17).$$

This step can eliminate the effect of the environment, so as to individually separate the phase term, which is shown as follows:

$$\frac{I_Y}{I_X} = \frac{4ab\sin(\phi_p - \phi_s)}{4ab\cos(\phi_p - \phi_s)} = \frac{\sin(\phi_p - \phi_s)}{\cos(\phi_p - \phi_s)} = \tan(\phi_p - \phi_s). \qquad (18)$$

Therefore, the phase difference $\Phi$ of the P polarized light and the S polarized light is obtained, which is shown as follows:

$$\Phi = \phi_p - \phi_s = \tan^{-1}\left(\frac{I_3 - I_4}{I_1 - I_2}\right). \qquad (19)$$

Figure 4:
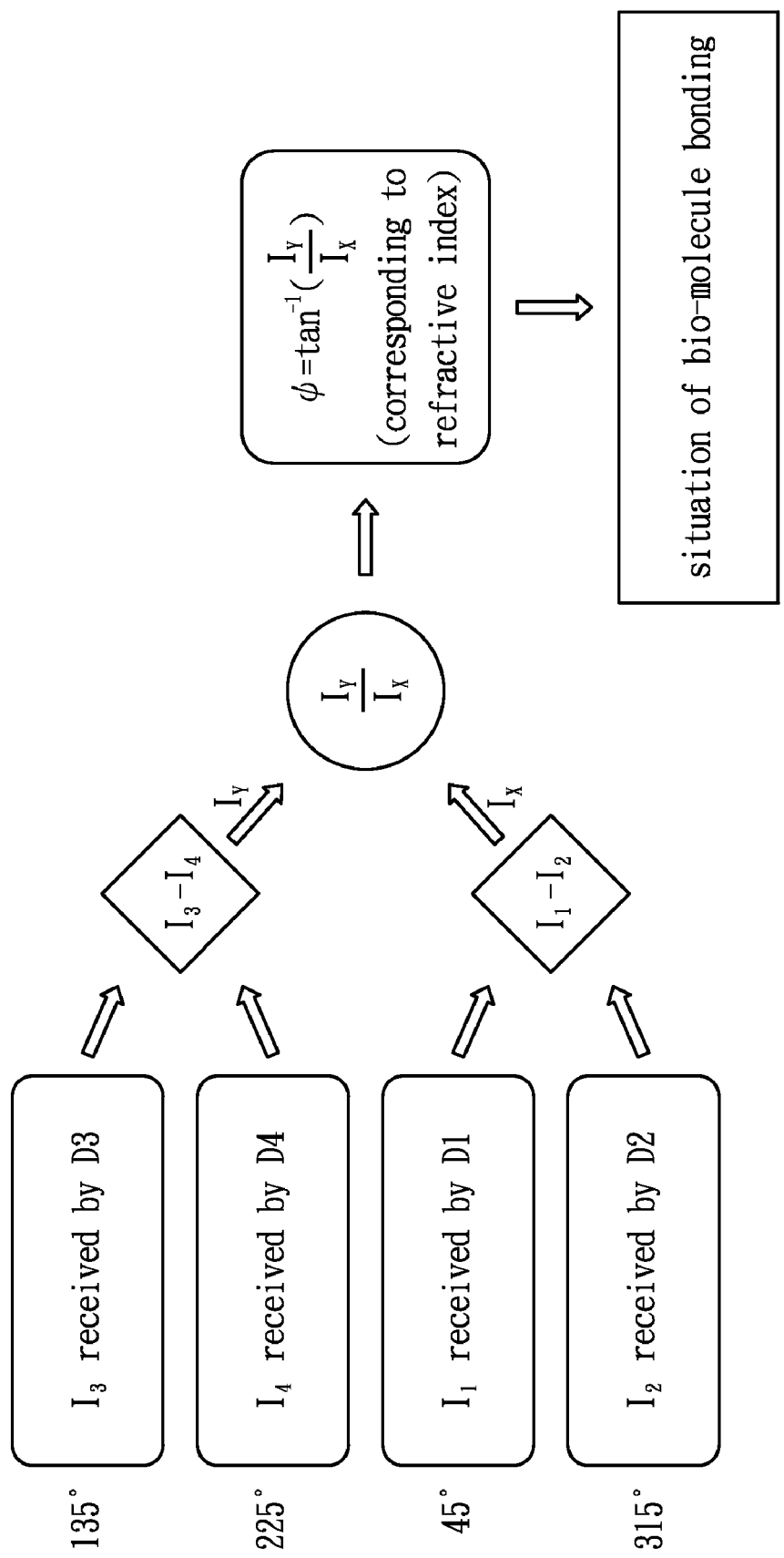
FIG. 4 shows the phase-resolving method in accordance with the present invention.

The steps of the phase-resolving variation are shown in FIG. 4.

(c) Simulation of Full-field Refractive Index Distribution

Figure 5:
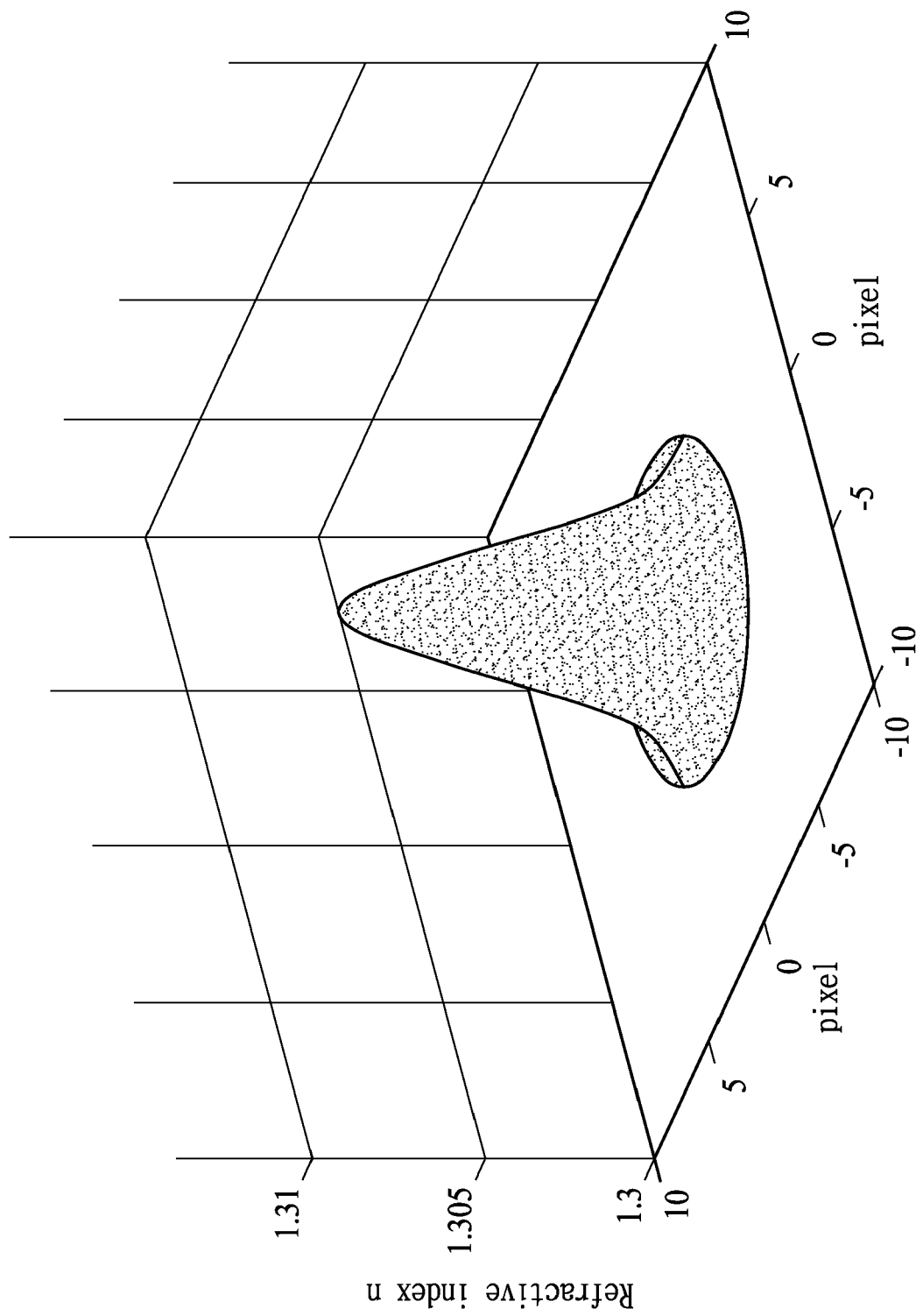
FIG. 5 shows a refractive index diagram of an object to be detected according to an embodiment of the present invention.
Figure 6A:
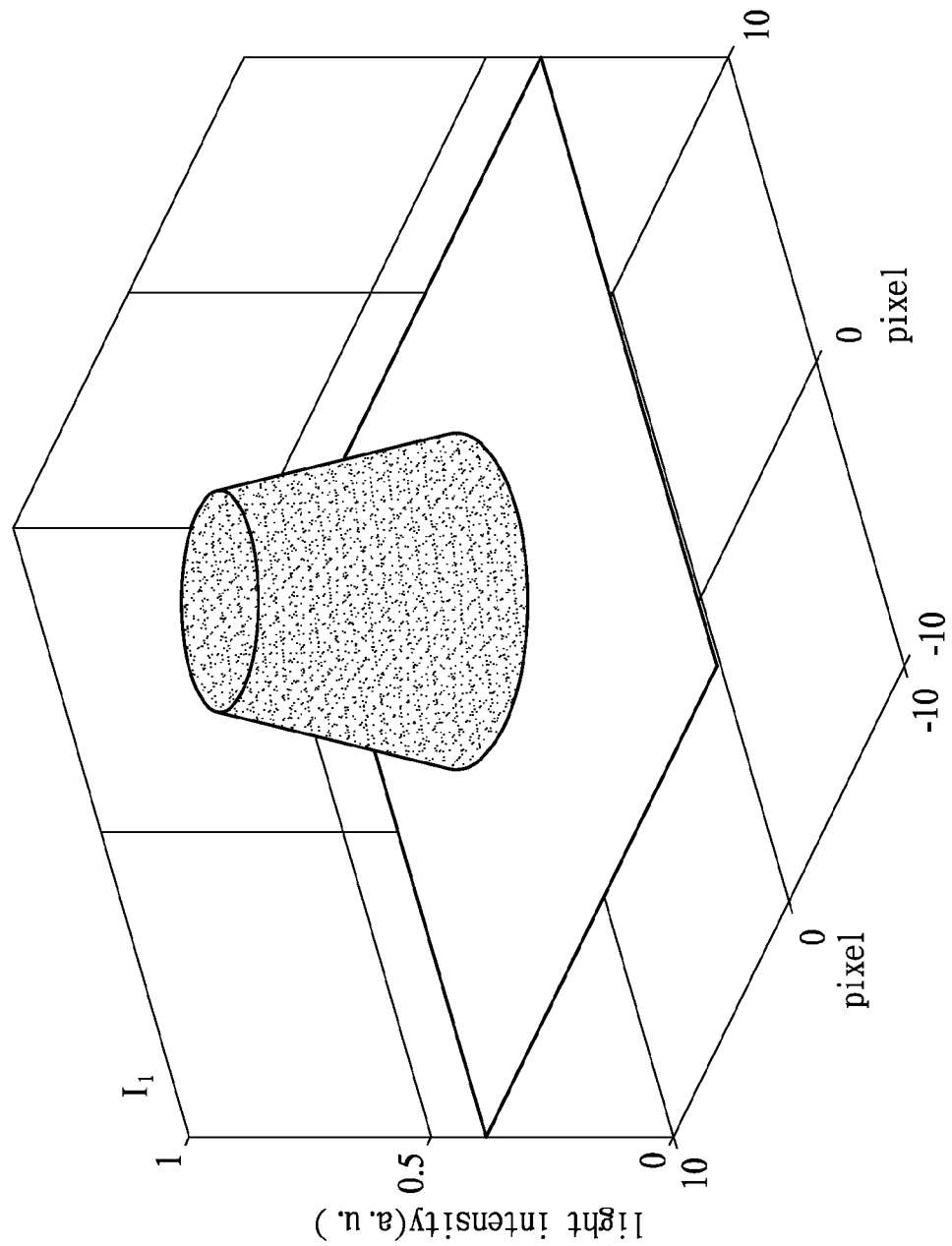
FIGS. 6(a) to 6(d) show intensity diagrams of a received light of the SPR detecting apparatus according to an embodiment of the present invention.
Figure 6B:
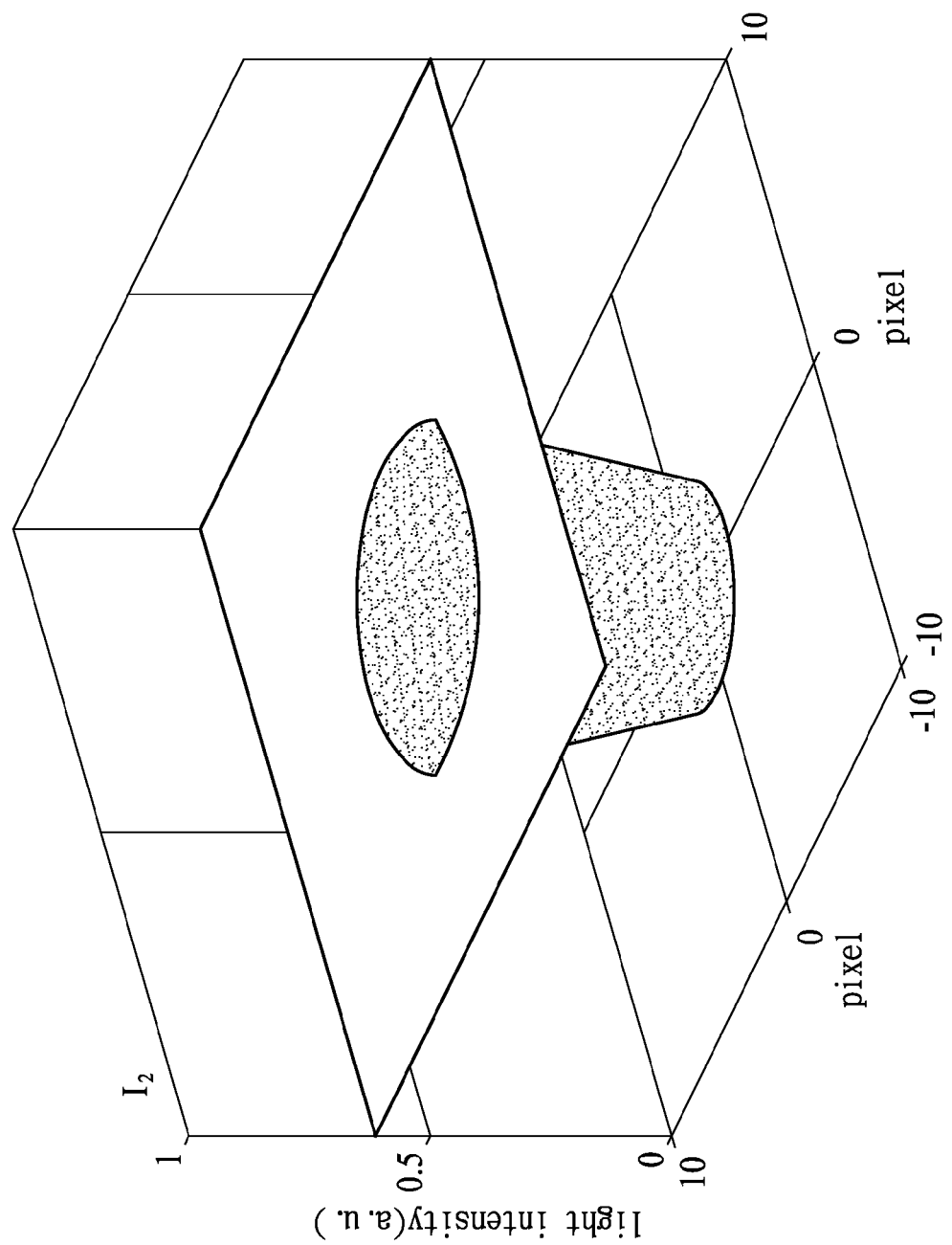
Figure 6C:
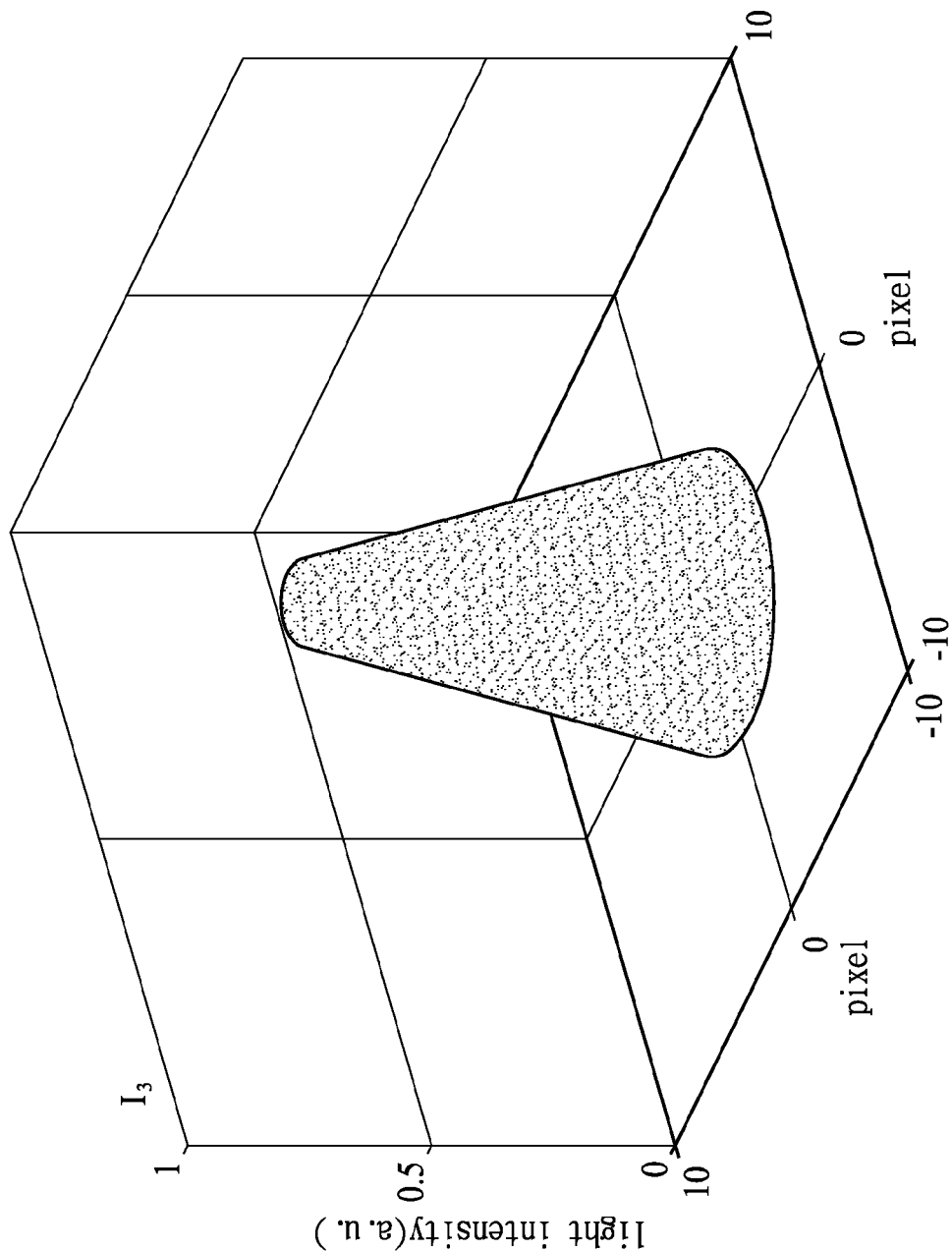
Figure 6D:
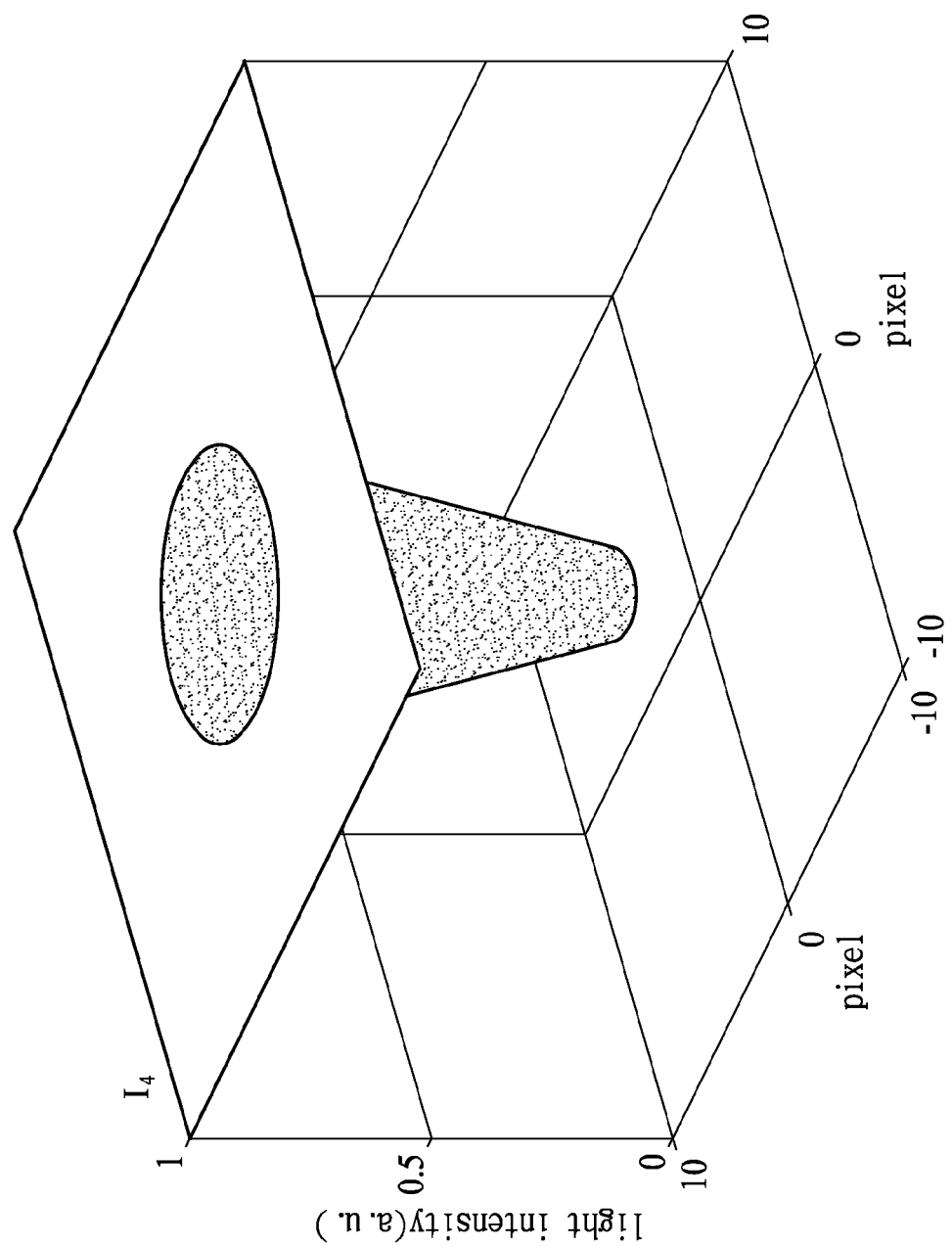
Figure 7:
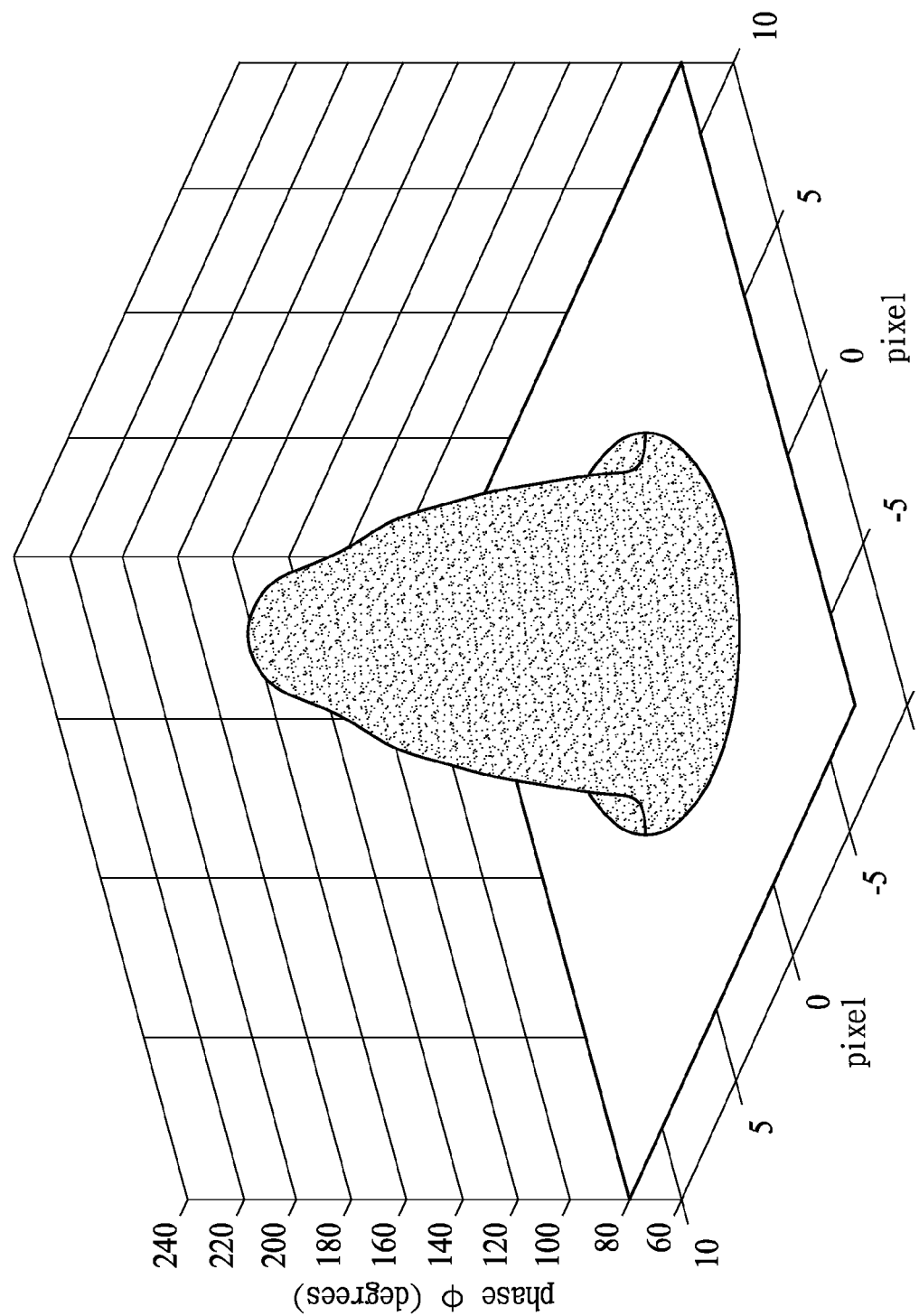
FIG. 7 shows a phase diagram of the SPR detecting apparatus according to the present invention.

The refractive index of an object to be detected forms in Gaussian distribution in space (the range of the refractive index variation: 1.30-1.31), as shown in FIG. 5. It is assumed that the simulation parameters in the architecture of FIG. 1 include the incident light wavelength of $\lambda$=785 nm, the incident angle of $\theta$=63.2 degrees, the metal (gold) film of a thickness of $d_2$=50 nm, and the dielectric constant of $\in_1$=2.27 and $\in_2$=−23.45+1.242i. As shown in FIGS. 6(a), 6(b), 6(c), and 6(d), the light intensity distributions of the four lights received by the four light detectors are obtained based on calculations of Equations (1) to (4) and Equations (9), (11), (13), and (15). The phase difference distribution shown in FIG. 7 is obtained through Equations (16) to (19). The feasibility of the present invention can be validated through computer simulation. It is found from FIGS. 5 and 7 that if the refractive index difference is 0.01 RIU, the corresponding phase variation is 156 degrees, which shows the high sensitivity of the phase-type SPR system. On the contrary, referring to FIG. 4 again, the variation of the refractive index n can be obtained by corresponding to the phase variation, so as to further deduce the status of objects to be detected, for example, the biomolecular binding.

Figure 8:
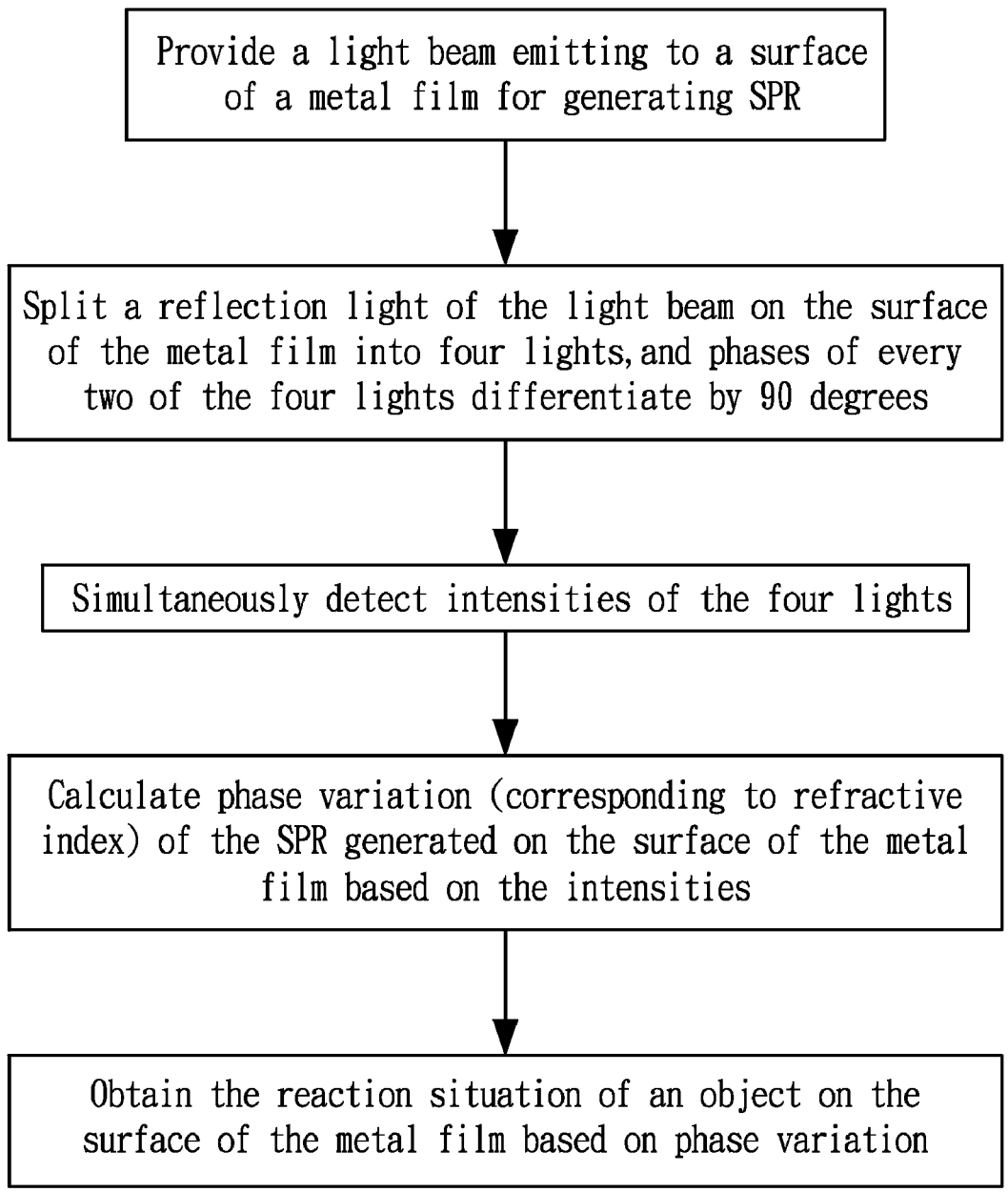
FIG. 8 is a flow chart of the SPR detection in accordance with the present invention.

In summary, the method for SPR detection of the present invention is shown in FIG. 8. First, a light beam emits into a surface of a metal film for generating SPR, and the reflection light of the light beam on the surface of the metal film is split into four lights, the phases of the four lights are classified into two groups, and two lights of each group differentiate by 90 degrees from each other. Then, the intensities of the four lights are detected, and the intensities are used to calculate phase variation of the SPR generated on the surface of the metal film. The phase variation can correspond to the refractive index variation of the metal film surface, i.e., the reaction status of the object to be detected on the metal film surface.

According to the present invention, no piezoelectric driving device is required, and the phases can be obtained without correction and compensation, so as to simplify the apparatus and reduce the cost. The SPR detection apparatus of the present invention generates measuring results through software, which can provide the user with the biomolecular reaction status information in real time.

The above-described embodiments of the present invention are intended to be illustrative only. Numerous alternative embodiments may be devised by those skilled in the art without departing from the scope of the following claims.

What is claimed is:

1. A surface plasmon resonance (SPR) detection apparatus, comprising:
   a light source for providing a light beam;
   a light-coupling unit having a surface of a metal film on which SPR is energized by the light beam emitting thereon;
   a phase-resolving module for splitting a reflection light of the light beam on the surface of the metal film into a first light, a second light, a third light, and a fourth light and detecting intensities of each light, wherein phases of the first light and the second light differentiate by 90 degrees, and phases of the third light and the fourth light differentiate by 90 degrees; and
   a data-processing unit for calculating phase variation of SPR on the surface of the metal film based on the intensities of the first light, second light, third light, and fourth light.

2. The SPR detection apparatus in accordance with claim 1, further comprising a polarizing plate located between the light source and the light-coupling unit for adjusting components of a P polarized light and an S polarized light of the light beam to increase contrast.

3. The SPR detection apparatus in accordance with claim 1, wherein the light-coupling unit further comprises an optical lens for generating the SPR in a Kretschmann coupling manner.

4. The SPR detection apparatus in accordance with claim 3, wherein the optical lens is a prism or a semi-cylindrical lens.

5. The SPR detection apparatus in accordance with claim 1, wherein the phase-resolving module comprises:
   a plurality of beam splitters for splitting the light beam into a first ray, a second ray, a third ray, and a fourth ray;
   a first analyzer with a polarizing angle of 45 degrees;
   a second analyzer with a polarizing angle of −45 degrees;
   at least one ¼ wave plate disposed between the plurality of beam splitters and the first analyzer and the second analyzer;
   wherein the first ray passes through the first analyzer to form the first light, the second ray passes through the second analyzer to form the second light, the third ray passes through the ¼ wave plate and the first analyzer to form the third light, and the fourth ray passes through the ¼ wave plate and the second analyzer to form the fourth light.

6. The SPR detection apparatus in accordance with claim 5, wherein a fast axis of the ¼ wave plate is 90 degrees.

7. The SPR detection apparatus in accordance with claim 5, wherein the phase-resolving module further comprises at least one reflecting mirror for changing a traveling direction of at least one of the first ray, the second ray, the third ray and the fourth ray.

8. The SPR detection apparatus in accordance with claim 5, wherein the phase-resolving module further comprises four light detectors for simultaneously detecting intensities of the first light, the second light, the third light and the fourth light.

9. The SPR detection apparatus in accordance with claim 1, further comprising a rotating mechanism to make sure an incident angle is equal to a reflection angle of the light beam on the surface of the metal film.

10. The SPR detection apparatus in accordance with claim 1, wherein the light source is a laser or a wideband light source.

11. The SPR detection apparatus in accordance with claim 1, wherein the data-processing unit is a computer or a microprocessor.

12. A surface plasmon resonance (SPR) detection method, comprising:
   providing a light beam emitting to a surface of a metal film for generating SPR;
   splitting a reflection light of the light beam on the surface of the metal film into four lights, and classifying phases of the four lights into two groups, wherein two lights in each group differentiate by 90 degrees;
   simultaneously detecting intensities of the four lights; and
   calculating phase variation of the SPR generated on the surface of the metal film based on the intensities.

13. The SPR detection method in accordance with claim 12, wherein the phase variation is obtained through the following equation:

$$\phi = \tan^{-1}\left(\frac{I_3 - I_4}{I_1 - I_2}\right),$$

wherein $\phi$ indicates a phase difference, and $I_1$, $I_2$, $I_3$, and $I_4$ respectively indicate the intensities of the four lights.

14. The SPR detection method in accordance with claim 12, wherein a combination of at least one beam splitter, at least one reflecting mirror, at least one ¼ wave plate, and at least one analyzer is utilized to split the reflection light of the light beam on the surface of the metal film into the four lights.

* * * * *